United States Patent
Faries, Jr. et al.

(10) Patent No.: US 8,148,667 B2
(45) Date of Patent: *Apr. 3, 2012

(54) THERMAL TREATMENT SYSTEM INSTRUMENT RACK AND METHOD OF SELECTIVELY THERMALLY TREATING MEDICAL INSTRUMENT PORTIONS

(75) Inventors: Durward I. Faries, Jr., Las Vegas, NV (US); Bruce R. Heymann, Vienna, VA (US); David Hendrix, Ashburn, VA (US)

(73) Assignee: Ecolab Inc., St. Paul, MN (US)

( * ) Notice: Subject to any disclaimer, the term of this patent is extended or adjusted under 35 U.S.C. 154(b) by 80 days.

This patent is subject to a terminal disclaimer.

(21) Appl. No.: 12/624,603

(22) Filed: Nov. 24, 2009

(65) Prior Publication Data

US 2010/0116810 A1    May 13, 2010

Related U.S. Application Data

(63) Continuation of application No. 11/320,645, filed on Dec. 30, 2005, now Pat. No. 7,671,302, which is a continuation-in-part of application No. 11/086,656, filed on Mar. 23, 2005, now Pat. No. 7,728,262.

(60) Provisional application No. 60/555,327, filed on Mar. 23, 2004.

(51) Int. Cl.
*A61B 19/00* (2006.01)
*A61B 19/10* (2006.01)
*F27B 11/00* (2006.01)
*A61F 7/00* (2006.01)

(52) U.S. Cl. ........ 219/429; 219/430; 219/433; 219/439; 604/114

(58) Field of Classification Search ................. None
See application file for complete search history.

(56) References Cited

U.S. PATENT DOCUMENTS

| 2,174,425 | A |   | 9/1939  | Schlumbohm |
|-----------|---|---|---------|------------|
| 2,323,356 | A |   | 7/1943  | Rosay      |
| 2,599,192 | A | * | 6/1952  | Miller ........................ 108/149 |
| 2,613,511 | A |   | 10/1952 | Walsh      |
| 2,807,701 | A |   | 9/1957  | Conlin et al. |
| 3,249,070 | A | * | 5/1966  | Day et al. ....................... 108/26 |
| 3,685,507 | A |   | 8/1972  | Donnelly   |

(Continued)

FOREIGN PATENT DOCUMENTS

JP    61185967    11/1986

(Continued)

*Primary Examiner* — Joseph M Pelham
(74) *Attorney, Agent, or Firm* — Edell, Shapiro & Finnan, LLC

(57) ABSTRACT

A system according to the present invention includes a cabinet, a basin positioned within the cabinet to contain and thermally treat a liquid bath, and a support assembly that stabilizes a surgical scope. The support assembly may include a first support that elevates scope optics above the liquid bath within the basin, and a second support that positions the shaft of the scope within the liquid bath, but above the floor and away from the walls of the basin. The scope optics resides outside of the bath in a dry state, while the remaining scope portions are positioned within the bath so the portions can be thermally treated. The support assembly enables a user to warm selected portions of the scope, while protecting the scope, the basin, and/or a drape lining the basin from damage caused when the scope contacts the basin.

32 Claims, 4 Drawing Sheets

U.S. PATENT DOCUMENTS

| | | | |
|---|---|---|---|
| 3,807,954 A | 4/1974 | McDonald | |
| 3,869,596 A | 3/1975 | Howie | |
| 3,902,484 A | 9/1975 | Winters | |
| 3,942,510 A | 3/1976 | Garrett | |
| 4,053,954 A | 10/1977 | Chapman | |
| 4,270,067 A | 5/1981 | Thomas et al. | |
| 4,284,880 A | 8/1981 | Keiser | |
| 4,393,659 A | 7/1983 | Keyes et al. | |
| 4,458,139 A | 7/1984 | McClean | |
| 4,474,016 A | 10/1984 | Winchell | |
| 4,516,564 A | 5/1985 | Koiso et al. | |
| 4,522,041 A | 6/1985 | Menzel | |
| 4,625,098 A | 11/1986 | Joe | |
| 4,782,835 A | 11/1988 | Bernardini | |
| 4,828,876 A | 5/1989 | Ohhara et al. | |
| 4,869,271 A | 9/1989 | Idris | |
| 4,903,710 A | 2/1990 | Jessamine et al. | |
| 4,934,152 A | 6/1990 | Templeton | |
| 4,967,061 A | 10/1990 | Weber, Jr. et al. | |
| 5,040,699 A | 8/1991 | Gangemi | |
| 5,042,455 A | 8/1991 | Yue et al. | |
| 5,042,981 A | 8/1991 | Gross | |
| RE33,854 E | 3/1992 | Adair | |
| 5,129,033 A | 7/1992 | Ferrara et al. | |
| 5,163,299 A * | 11/1992 | Faries et al. | 62/66 |
| 5,174,306 A | 12/1992 | Marshall | |
| 5,310,524 A | 5/1994 | Campbell et al. | |
| 5,331,820 A | 7/1994 | Faries, Jr. et al. | |
| 5,333,326 A | 8/1994 | Faries, Jr. et al. | |
| 5,345,063 A | 9/1994 | Reusche et al. | |
| 5,351,675 A | 10/1994 | Brodsky | |
| 5,363,746 A | 11/1994 | Gordon | |
| 5,374,278 A | 12/1994 | Chesterfield et al. | |
| 5,374,813 A | 12/1994 | Shipp | |
| 5,383,476 A | 1/1995 | Peimer et al. | |
| 5,386,835 A | 2/1995 | Elphick et al. | |
| 5,396,905 A | 3/1995 | Newman et al. | |
| 5,400,267 A | 3/1995 | Denen et al. | |
| 5,400,616 A | 3/1995 | Faries, Jr. et al. | |
| 5,402,644 A | 4/1995 | Faries, Jr. et al. | |
| 5,429,801 A | 7/1995 | Faries, Jr. et al. | |
| 5,435,322 A * | 7/1995 | Marshall | 128/849 |
| 5,443,082 A | 8/1995 | Mewburn | |
| 5,449,892 A | 9/1995 | Yamada | |
| 5,457,962 A | 10/1995 | Faries, Jr. et al. | |
| 5,463,213 A | 10/1995 | Honda | |
| 5,480,302 A | 1/1996 | Fife | |
| 5,502,980 A | 4/1996 | Faries, Jr. et al. | |
| 5,517,170 A | 5/1996 | Peters et al. | |
| 5,518,502 A | 5/1996 | Kaplan et al. | |
| 5,522,095 A | 6/1996 | Faries, Jr. et al. | |
| 5,522,805 A | 6/1996 | Vancaillie et al. | |
| 5,524,478 A | 6/1996 | Joy et al. | |
| 5,524,643 A | 6/1996 | Faries, Jr. et al. | |
| 5,531,697 A | 7/1996 | Olsen et al. | |
| 5,539,185 A * | 7/1996 | Polster | 219/439 |
| 5,549,543 A | 8/1996 | Kim | |
| 5,551,240 A | 9/1996 | Faries, Jr. et al. | |
| 5,615,423 A | 4/1997 | Faries, Jr. et al. | |
| 5,647,840 A | 7/1997 | D'Amelio et al. | |
| 5,651,757 A | 7/1997 | Meckstroth | |
| 5,653,938 A | 8/1997 | Faries, Jr. et al. | |
| 5,658,478 A | 8/1997 | Roeschel et al. | |
| 5,664,582 A | 9/1997 | Szymaitis | |
| 5,715,547 A * | 2/1998 | Becker et al. | 4/619 |
| 5,717,188 A | 2/1998 | Vaillancourt | |
| 5,800,352 A | 9/1998 | Ferre et al. | |
| 5,809,788 A | 9/1998 | Faries, Jr. et al. | |
| 5,816,252 A | 10/1998 | Faries, Jr. et al. | |
| 5,857,467 A | 1/1999 | Faries, Jr. et al. | |
| 5,862,672 A | 1/1999 | Faries, Jr. et al. | |
| 5,879,621 A | 3/1999 | Faries, Jr. et al. | |
| 5,910,106 A | 6/1999 | Morgan et al. | |
| 5,950,438 A | 9/1999 | Faries, Jr. et al. | |
| D417,809 S | 12/1999 | Hofman | |
| 6,003,328 A | 12/1999 | Faries, Jr. et al. | |
| 6,035,855 A | 3/2000 | Faries, Jr. et al. | |
| 6,087,636 A * | 7/2000 | Faries, Jr. et al. | 219/429 |
| 6,091,058 A | 7/2000 | Faries, Jr. et al. | |
| 6,102,044 A | 8/2000 | Naidyhorski | |
| D441,996 S | 5/2001 | Wright | |
| 6,231,596 B1 | 5/2001 | Collins | |
| 6,234,635 B1 | 5/2001 | Seitzinger et al. | |
| 6,255,627 B1 | 7/2001 | Faries, Jr. et al. | |
| 6,259,067 B1 | 7/2001 | Faries, Jr. et al. | |
| D447,900 S | 9/2001 | Wright | |
| 6,341,704 B1 | 1/2002 | Michel, Jr. | |
| 6,371,121 B1 | 4/2002 | Faries, Jr. et al. | |
| 6,448,571 B1 | 9/2002 | Goldstein | |
| 6,586,950 B1 | 7/2003 | Sargent et al. | |
| 6,593,552 B1 | 7/2003 | Li | |
| 6,644,383 B2 | 11/2003 | Joseph et al. | |
| 6,701,174 B1 | 3/2004 | Krause et al. | |
| 6,810,881 B2 | 11/2004 | Faries, Jr. et al. | |
| 6,860,271 B2 | 3/2005 | Faries, Jr. et al. | |
| 6,884,970 B2 | 4/2005 | Lehman | |
| 6,910,485 B2 | 6/2005 | Faries, Jr. et al. | |
| 6,918,395 B2 | 7/2005 | Faries, Jr. et al. | |
| 6,927,365 B2 | 8/2005 | Li | |
| 7,041,941 B2 | 5/2006 | Faries, Jr. et al. | |
| 7,128,275 B2 | 10/2006 | Kammer et al. | |
| 7,176,030 B2 | 2/2007 | Faries, Jr. et al. | |
| 7,276,675 B2 | 10/2007 | Faries, Jr. et al. | |
| 7,307,245 B2 | 12/2007 | Faries, Jr. et al. | |
| 7,309,472 B2 * | 12/2007 | Michaelson et al. | 422/297 |
| 7,311,660 B2 | 12/2007 | Gomez | |
| 7,347,210 B2 | 3/2008 | Faries, Jr. et al. | |
| 7,350,373 B1 | 4/2008 | Faries, Jr. et al. | |
| 7,417,205 B2 | 8/2008 | Faries, Jr. et al. | |
| 7,418,966 B2 | 9/2008 | Faries, Jr. et al. | |
| 7,671,302 B1 * | 3/2010 | Faries et al. | 219/429 |
| 7,728,262 B1 | 6/2010 | Faries, Jr. et al. | |
| 7,854,230 B2 | 12/2010 | Faries, Jr. et al. | |
| 7,959,860 B2 | 6/2011 | Faries, Jr. et al. | |
| 2003/0132216 A1 | 7/2003 | Li | |
| 2003/0231990 A1 | 12/2003 | Faries, Jr. et al. | |
| 2004/0200480 A1 | 10/2004 | Faries, Jr. et al. | |
| 2004/0200483 A1 | 10/2004 | Faries, Jr. et al. | |
| 2004/0208780 A1 | 10/2004 | Faries, Jr. et al. | |
| 2005/0247169 A1 | 11/2005 | Faries et al. | |
| 2006/0065276 A1 | 3/2006 | Kammer et al. | |
| 2006/0086361 A1 | 4/2006 | Kammer et al. | |
| 2006/0091128 A1 | 5/2006 | Kammer et al. | |
| 2006/0091129 A1 | 5/2006 | Colonna | |
| 2006/0194324 A1 | 8/2006 | Faries et al. | |
| 2006/0260443 A1 | 11/2006 | Faries et al. | |
| 2006/0289445 A1 | 12/2006 | Colonna | |
| 2007/0089753 A1 | 4/2007 | Faries et al. | |
| 2009/0255540 A1 | 10/2009 | Faries, Jr. | |
| 2010/0116810 A1 * | 5/2010 | Faries, Jr. et al. | 219/429 |
| 2010/0200561 A1 | 8/2010 | Faries, Jr. et al. | |
| 2011/0270367 A1 | 11/2011 | Faries, Jr. et al. | |

FOREIGN PATENT DOCUMENTS

| | | |
|---|---|---|
| JP | 06123532 | 5/1994 |

* cited by examiner

THERMAL TREATMENT SYSTEM INSTRUMENT RACK AND METHOD OF SELECTIVELY THERMALLY TREATING MEDICAL INSTRUMENT PORTIONS

CROSS REFERENCE TO RELATED APPLICATIONS

The present application is a continuation of U.S. application Ser. No. 11/320,645 entitled "Thermal Treatment System Instrument Rack and Method of Selectively Thermally Treating Medical Instrument Portions" and filed Dec. 30, 2005, now issued as U.S. Pat. No. 7,671,302, which is a continuation-in-part of U.S. application Ser. No. 11/086,656 entitled "Thermal Treatment System Instrument Rack and Method of Selectively Thermally Treating Medical Instrument Portions" and filed Mar. 23, 2005, now issued as U.S. Pat. No. 7,728,262, which, in turn, claims priority from U.S. Provisional Patent Application Ser. No. 60/555,327, entitled "Thermal Treatment System Instrument Rack and Method of Selectively Thermally Treating Medical Instrument Portions" and filed Mar. 23, 2004. The disclosures of all of these documents are incorporated herein by reference in their entireties.

BACKGROUND OF THE INVENTION

1. Field of the Invention

The present invention pertains to a system for thermally treating surgical instruments. In particular, the present invention pertains to a system for warming surgical scopes in a temperature controlled liquid bath while maintaining optics of the scope in a dry state.

2. Discussion of the Related Art

Surgical scopes (e.g., laparoscopes, endoscopes, arthroscopes, etc.) are used in corrective medical procedures, as well as in medical procedures that image interior viscera such as surfaces of the stomach, small intestines, and colon. The use of surgical scopes permits a surgeon to view a patient body interior with a minimal amount of cutting of patient tissue. The surgical scopes may be warmed prior to use, where scope optics must remain dry to protect those optics and prevent distortion of the image. The scopes are warmed for several reasons, including enhancing image results, preventing infections, and maintaining normothermia. For example, a scope that is unwarmed prior to being inserted into a patient body may fog due to differences between the body temperature and scope temperature, thereby impeding or distorting the resulting image. Further, scopes may be warmed to minimize trauma caused to tissue in response to insertion of the scope into the patient body. The trauma basically results from the temperature difference between the scope and the tissue. Inserting a hot or cold scope may damage tissue, thereby leading to infections. Inserting a cold scope may also lower core body temperature, thereby leading to hypothermia and compromising patient safety.

Currently, scopes are typically warmed in an insulated container (e.g., THERMOS) filled with warm liquid. However, since the container generally does not provide temperature control for the liquid and/or scopes, the temperature of the scope is not precisely known by medical personnel. Accordingly, medical personnel may utilize scopes at inadequate temperatures relative to a patient body, thereby potentially causing tissue trauma, fogging of the scope as described above, and/or hypothermia. A chemical wipe or spray may be used to reduce fogging instead of warming the scopes; however, the chemical may be inadvertently introduced into the patient, thereby causing complications. In addition, when an insulated container is used, the scope may be damaged when it, by necessity, comes in contact with the sides and/or bottom of the container.

OBJECTS AND SUMMARY OF THE INVENTION

Accordingly, it is an object of the present invention to selectively treat portions of a surgical instrument with a temperature controlled thermal bath.

It is another object of the present invention to maintain the optics of a surgical scope disposed in a thermal treatment system basin in a dry state supporting the optics above heated surgical liquid.

Yet another object of the present invention is to elevate portions of a surgical instrument above the basin of a temperature controlled thermal bath while selectively treating other portions of the surgical instrument immersed in the bath.

A further object of the present invention is to prevent damage to a surgical instrument placed within a thermal bath that selectively treats portions of the surgical instrument, as well as to prevent damage to the basin of a thermal treatment system that controls the temperature of the thermal bath and/or a surgical drape disposed over the basin.

A still further object of the present invention is to prevent damage to the surgical instrument, the basin of a thermal treatment system, and/or the surgical drape by supporting the optics portion of the instrument above the thermal bath by using a first support member and by supporting the operative portion of the instrument within the thermal bath and above the floor of the basin using a second support member.

A still further object of the present invention is to prevent puncturing of the surgical drape, which could cause a breach in the sterile field maintained by the drape.

According to the present invention, a system includes a cabinet, a basin positioned within the cabinet to contain and thermally treat a liquid bath, a first support member disposed on the cabinet that supports exposed scope optics above the liquid bath, and a second support member that supports the operative portion of the scope such that it is submerged within the liquid and supported above the floor of the basin. With this configuration, the scope optics resides outside of the bath in a dry state, thereby permitting the remaining scope portions within the bath to be thermally treated. This enables accurate temperature warming of the scope to reduce trauma of tissue, enables retrieval of enhanced images by the scope during a medical procedure, and maintains normothermia. In addition, greater protection is afforded the scope, the basin, and/or a drape disposed over the basin since the support members stabilize the scope, preventing contact between the scope and basin. The present invention permits medical personnel or operating room staff to warm scopes in a controlled environment while maintaining scope optics in a dry state.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION OF THE PREFERRED EMBODIMENTS

Figure 1:
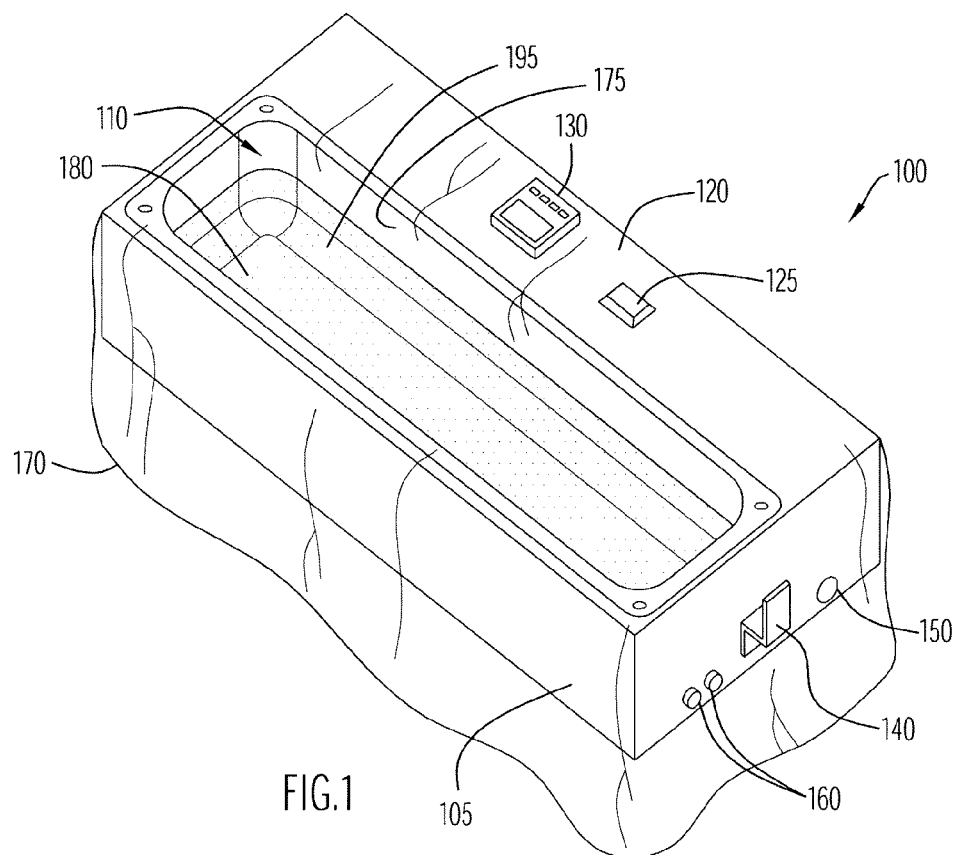
FIG. 1 illustrates a perspective view of a thermal treatment system in accordance with one embodiment of the present invention.

An exemplary system for thermally treating a sterile medium (e.g., solution or liquid) is illustrated in FIG. 1. As shown, the thermal treatment system 100 includes a cabinet or housing 105 in the form of a generally rectangular block and a warming basin 110 recessed into the top surface 120 of the cabinet 105. The basin 110 may be of any size and/or shape; however, by way of example only, the basin is illustrated having a substantially rectangular shape including an open top structure with generally vertical side walls 175 extending up from a generally horizontal floor 180. A heater power switch 125 and a temperature controller/indicator 130 are provided on the top surface 120 of the cabinet 105, adjacent the warming basin 110. A support hook 140 is disposed on the cabinet front wall (e.g., as viewed in FIG. 1) and may support a system power cord (not shown). Electrical connections may be made to the cabinet 105 via a power port 150 disposed on the cabinet front wall adjacent the hook 140. In addition, fuse receptacles 160 may be disposed on the cabinet front wall proximate the hook 140 to receive fuses in order to prevent damage to circuitry (such as the circuitry similar to that illustrated in FIG. 2) contained within the cabinet 105.

Figure 7:
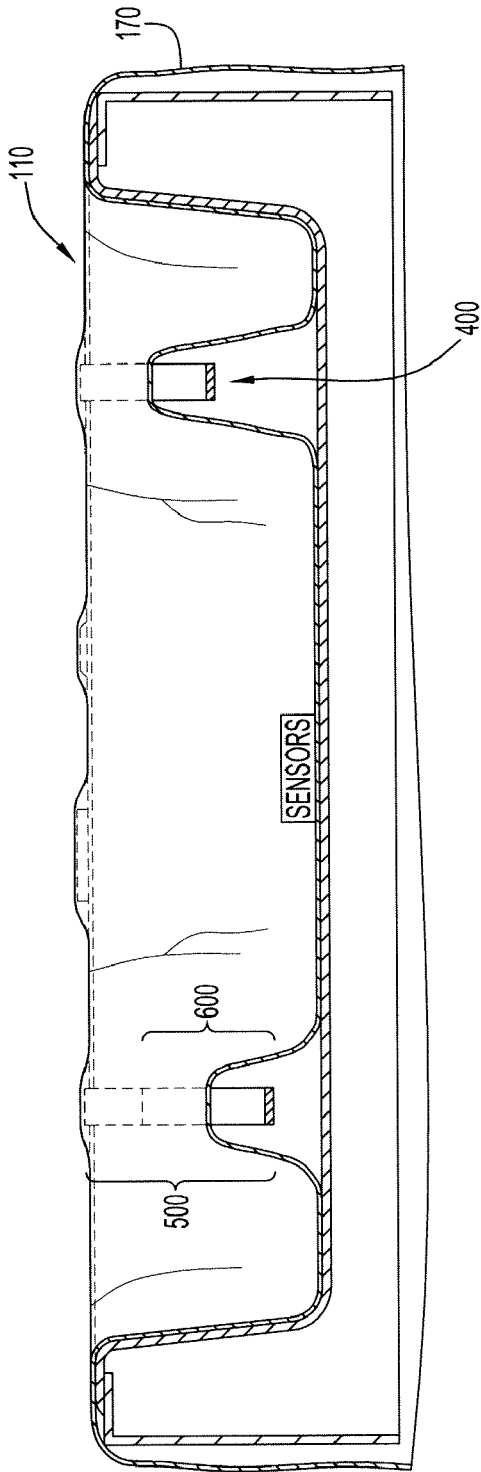
FIGS. 7-8 illustrate views in partial section of the support assemblies for a surgical instrument of FIGS. 3-6, showing the support assemblies below the drape.
Figure 8:
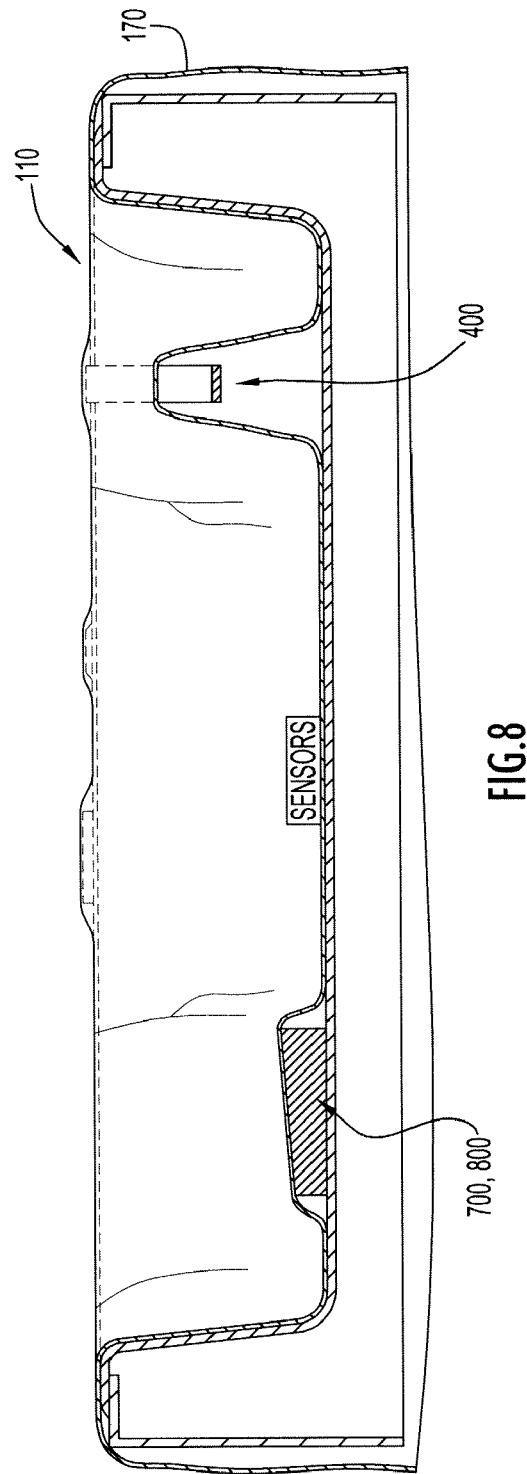

A sterile drape 170, preferably transparent, may be disposed over the top and sides of cabinet 105. The power switch 125 and the controller 130, disposed on the top surface 120 of the cabinet 105, are actuable manually through drape 170. The portion of the drape 170 disposed as a liner in the basin 110 serves as a sterile container or receptacle for a sterile medium 195 to be heated and placed therein. The sterile medium 195 treated by the thermal treatment system 100 may include, but is not limited to, sterile liquid comprising a 0.80% to 0.95% sodium chloride solution (i.e., saline). The drape 170 is preferably transparent and may be made from a material that is impervious to the sterile liquid and sufficiently soft and pliable to conform to the walls 175 and floor 180 of the basin 110. The thickness of the drape 170 is preferably minimized to render thermal transfer therethrough most efficient, yet the thickness is sufficient to resist tearing and puncturing during normal use. The drape 170 may be made of materials commonly used in hospitals for surgical drapes and has a thickness, by way of example only, of approximately 4.5 to 6.0 mils. The drape 170, however, may have any desired thickness. The drape 170 may also be made of polyurethane film as disclosed for the drape in U.S. Pat. No. 4,934,152 (Templeton), the disclosure of which is incorporated herein by reference in its entirety. In addition, the drape 170 may include sensors (FIGS. 7-8) to detect the presence or absence of liquid within the basin and/or the presence of a drape leak. Examples of these types of drapes are disclosed in U.S. Pat. No. 6,810,881 (Faries, Jr. et al.) and U.S. Pat. No. 6,910,485 (Faries, Jr. et al.); as well as in U.S. Published Patent Application Nos. 2003/0231990 (Faries, Jr. et al.), 2004/0200483 (Faries, Jr. et al.), 2004/0200480 (Faries, Jr. et al.), and 2004/0208780 (Faries, Jr. et al.), the disclosures of which are incorporated herein by reference in their entireties.

The drape 170 may further include a preformed container portion (not shown) contoured to match the contour of the basin 110. The preformed container portion is typically thicker than the remaining portions of the drape described above in order to resist puncture and enable the container portion to maintain the shape of the basin 110. By way of example only, the container portion may be made of a heavy gauge polyethylene/ionomer resin blend having a thickness of approximately 10 to 16 mils. The percentage of ionomer resin in the blend is in the approximate range of forty to seventy percent. The drapes described above are designed to be disposable after a single use and are provided pre-sterilized and prepackaged in a manner to preserve its sterile state during storage.

The drape 170 is typically positioned over thermal treatment system 100 such that a portion of the drape is disposed in the basin 110 to form a drape receptacle. The drape 170 forms a sterile field above the basin to maintain sterility of a sterile liquid 195 placed in the drape receptacle. Generally, objects (e.g., medical instruments, containers, etc.) may be warmed in the basin by placing the objects in the heated liquid within the basin 110 (and contained by the drape receptacle).

Figure 2:
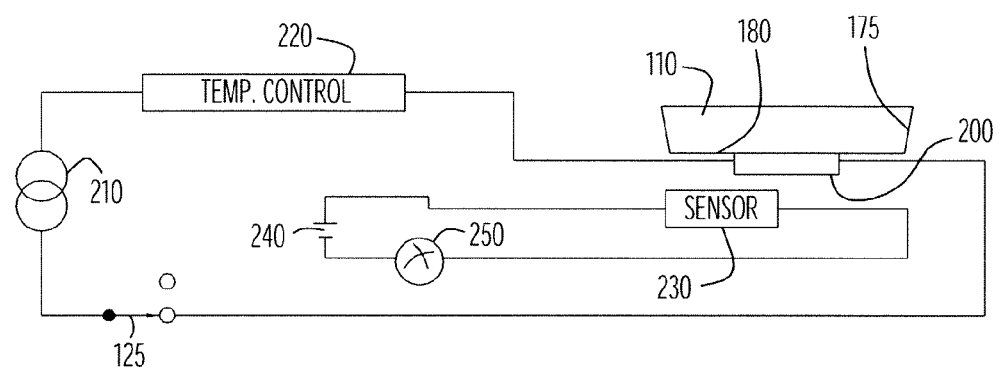
FIG. 2 illustrates an electrical schematic diagram of the heating unit employed by the thermal treatment system of FIG. 1.

The manner of heating sterile liquid in the warming basin 110 is illustrated schematically in FIG. 2. An electrical circuit includes a power source 210 connected in series with a temperature control unit 220, a heater element or pad 200, and the power control switch 125 (also illustrated in FIG. 1). The heater element 200 is typically a thin, wafer-like member disposed along the bottom surface of the warming basin 110, secured to the basin by a suitable pressure sensitive adhesive having efficient heat transfer characteristics. The heater element 200 has smaller dimensions than those of the basin floor 180 and is disposed at the approximate center of the basin bottom surface. Alternatively, the heater element 200 may be of any quantity (e.g., at least one), shape or size, and may include any configuration (e.g., strips, bars, segments, etc.) that covers the entirety or any portion of the basin 110. In addition, the heater element 200 may be implemented by any conventional or other type of heater or heating element (e.g., heating coils, etc.) that may be disposed on the basin at any suitable locations.

The temperature control unit 220 includes a device for adjusting current passing through heater element 200 so as to permit selective adjustment of the heat applied to the basin 110 (and thus the liquid in the basin). The power switch 125 permits selective application and removal of current flow with respect to the heater element 200. The heater element 200 is controlled by the controller 220 in accordance with an entered desired temperature and temperatures measured by a temperature sensor 230. The temperature sensor 230 is preferably implemented by a conventional resistive temperature device (RTD) (e.g., a 1,000 Ohm RTD). The sensor 230, however, may be implemented by any conventional or other type of temperature sensor, and may be disposed at any suitable location on the basin or within the cabinet 105. By way of example only, the temperature sensor 230 may be disposed adjacent the basin 110 to sense the temperature of the basin, the liquid contained therein, and/or the heater element 200. The sensor 230 is connected in series with a voltage source 240 and an indicator 250. The voltage source 240 and the power source 210 may be the same source, or the voltage for one may be derived from the other. The indicator 250 measures the current through temperature sensor 230, with the current being proportional to the sensed temperature. Both the indicator 250 and temperature controller 220 may correspond, for example, to the temperature controller/indicator 130 described above. For further examples of these types of heating units, reference is made to U.S. Pat. No. 5,333,326 (Faries, Jr. et al.) and U.S. Pat. No. 6,087,636 (Faries, Jr. et al.), the disclosures of which are incorporated herein by reference in their entireties.

It is to be understood that the thermal treatment system 100 described above and illustrated in FIG. 1 may have various configurations. For example, the thermal treatment system 100 may be configured to cool and/or congeal the medium to produce cooled liquid or surgical slush. In this instance, the heater element 200 may be replaced by refrigeration devices that are controlled in substantially the same manner described above. Furthermore, the thermal treatment system 100 may include a plurality of basins warming and/or cooling a sterile medium as described above. In addition, the system may be configured to attach to a stand or another system cabinet or may be configured as a stand-alone unit. Examples of these types of system configurations are disclosed in U.S. Pat. No. 5,333,326 (Faries, Jr. et al.); U.S. Pat. No. 5,429,801 (Faries, Jr. et al.); U.S. Pat. No. 5,522,095 (Faries, Jr. et al.); U.S. Pat. No. 5,524,643 (Faries, Jr. et al.); U.S. Pat. No. 5,615,423 (Faries, Jr. et al.); U.S. Pat. No. 5,653,938 (Faries, Jr. et al.); U.S. Pat. No. 5,816,252 (Faries, Jr. et al.); U.S. Pat. No. 5,862,672 (Faries, Jr. et al.); U.S. Pat. No. 5,857,467 (Faries, Jr. et al.); U.S. Pat. No. 5,879,621 (Faries, Jr. et al.); U.S. Pat. No. 6,091,058 (Faries, Jr. et al.); and/or U.S. Pat. No. 6,255,627 (Faries, Jr. et al). The disclosures of the above-mentioned patents are incorporated herein by reference in their entireties.

Figure 3:
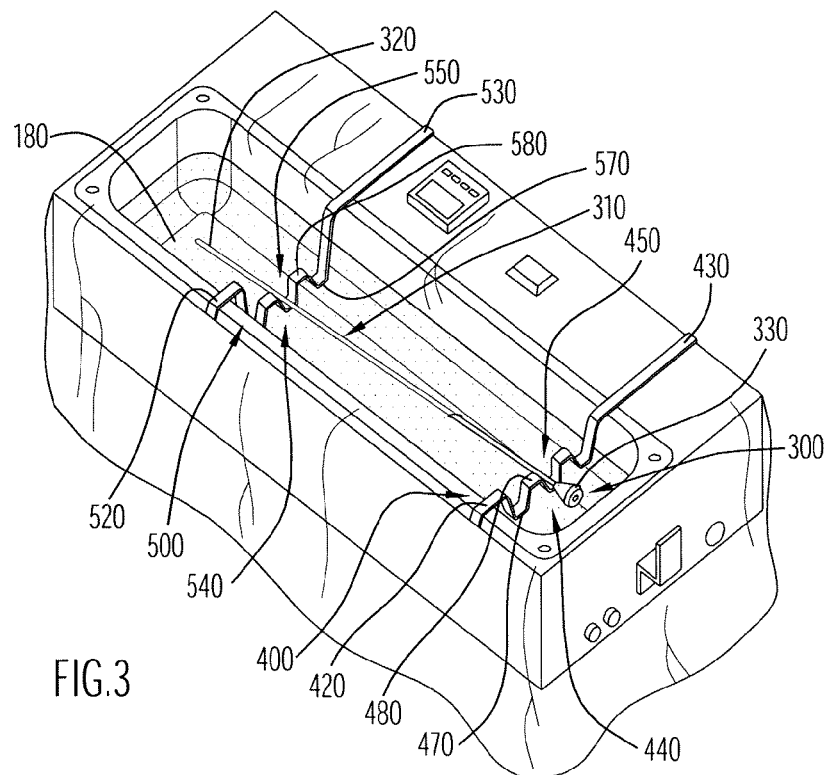
FIG. 3 illustrates a perspective view of a support assembly for a surgical instrument according to one embodiment of the invention, showing the support assembly coupled to the thermal treatment system of FIG. 1.

The above described thermal system 100 may be utilized to heat a medical instrument such as a surgical scope. Surgical scopes (e.g., laparoscopes, endoscopes, arthroscopes, etc.) are used in corrective medical procedures, as well as in medical procedures that image interior viscera such as surfaces of the stomach, small intestines, and colon. The use of surgical scopes permits a surgeon to view a patient body interior with a minimal amount of cutting of patient tissue. Referring to FIG. 3, a conventional or other surgical scope 300 typically includes a shaft member 310 with a distal portion 320 for insertion into a patient body. The distal portion 320 typically includes a lens operable to capture and transmit images. An optics unit 330 (e.g., a lens, etc.) is disposed on the proximal end of the shaft member 310. Fiber optics (not shown) generally extend along the interior of the shaft member 310 to transmit image data from the distal end of the scope to the optics unit 330 for conveyance to the surgeon (e.g., via an eyepiece, camera, or other device that may be coupled to the optics unit 330).

When surgical scopes 300 are warmed prior to use, the scope optics (i.e., the optics unit 330) must remain dry to protect those optics and prevent distortion of the image. Currently, scopes 300 are typically warmed in an insulated container (e.g., a THERMOS container) filled with warm liquid without temperature control. During treatment, the scopes come into contact with the sides and/or bottom of the container. The scopes 300 are warmed for several reasons, including enhancing image results, preventing infections, and maintaining normothermia. For example, a scope that is unwarmed prior to being inserted into a patient body may fog due to differences between the body temperature and scope temperature, thereby impeding or distorting the resulting image. Further, scopes may be warmed to minimize trauma caused to tissue in response to insertion of the scope into the patient body. The trauma basically results from the temperature difference between the scope and the tissue. Inserting a hot or cold scope may damage tissue, thereby leading to infections. Inserting a cold scope may lower the core body temperature of a patient, leading to hypothermia. A chemical wipe or spray may alternatively be used to reduce fogging; however, the chemical may be inadvertently introduced into the patient, thereby causing complications.

Accordingly, the present invention enables medical personnel (e.g., operating room staff, etc.) to warm scopes 300 in a controlled environment (e.g., liquid bath) while maintaining the scope optics 330 in a dry state. In addition, the present invention provides a support system that stabilizes the scope, preventing its contact with any hard surface such as the walls or floor of basin holding the liquid bath. In particular, the thermal treatment system 100 may include a support assembly comprising a first support member 400 and a second support member 500. The first support member 400 is operable to elevate optics unit 330 above the surface (fluid line) of the temperature-controlled, liquid bath contained in the basin 110. The second support member 500 is operable to position at least a portion of the scope distal portion 320 below the surface (fluid line) of the liquid bath, and above the floor 180 and away from the sides of the basin 110. With this configuration, the assembly is adapted to position at least one portion of the shaft member 310 within the liquid for thermal treatment, while safely maintaining the optics unit 330 in a dry state.

The first support member 400 may comprise a tray or rack configured to support the optics unit over the thermal bath. As illustrated in FIG. 3, the first support member 400 (also called a first support rack) may comprise a bar including a first end portion 420, a second end portion 430, and an intermediate portion 440 that includes at least one receptacle 450 operable to receive a corresponding surgical scope 300. The first support rack 400 may be of any shape or size, and may include any number of receptacles 450. Similarly, the bar may be of any size, shape, or thickness appropriate to its described function, and may include any suitable cross-sectional shape. By way of example only, the bar may be a substantially flat bar with a substantially rectangular cross section. The receptacles 450 may each be of any shape suitable to secure a corresponding scope 300 therein, while elevating the optics unit 330 of the scope above the liquid bath contained within the basin 110. By way of further example, the intermediate portion 440 may include a series of serpentine or undulate portions that form the receptacles 450. The undulate portions are formed by a series of alternating recesses 470 and peaks 480. The recesses 470 form the receptacles 450 that support the optics units 330 of the corresponding scopes 300. The receptacles 450 may include dimensions slightly larger than those of the shaft member 310, but smaller than those of the optics unit 330. This configuration enables the scope 300 to be readily placed into and removed from the receptacle 450 (and thus the thermal bath), while the optics unit 330 may serve as a stop to prevent the scope from sliding into liquid filled basin 110. The first support rack 400 may be constructed of high-density polyethylene, ABS thermoplastic, metals or steel, propylene material, or any material that is capable of withstanding temperatures typically used in thermal treatment systems (e.g., at least about 160° F.) and is sufficiently rigid to hold objects placed thereon.

Figure 4:
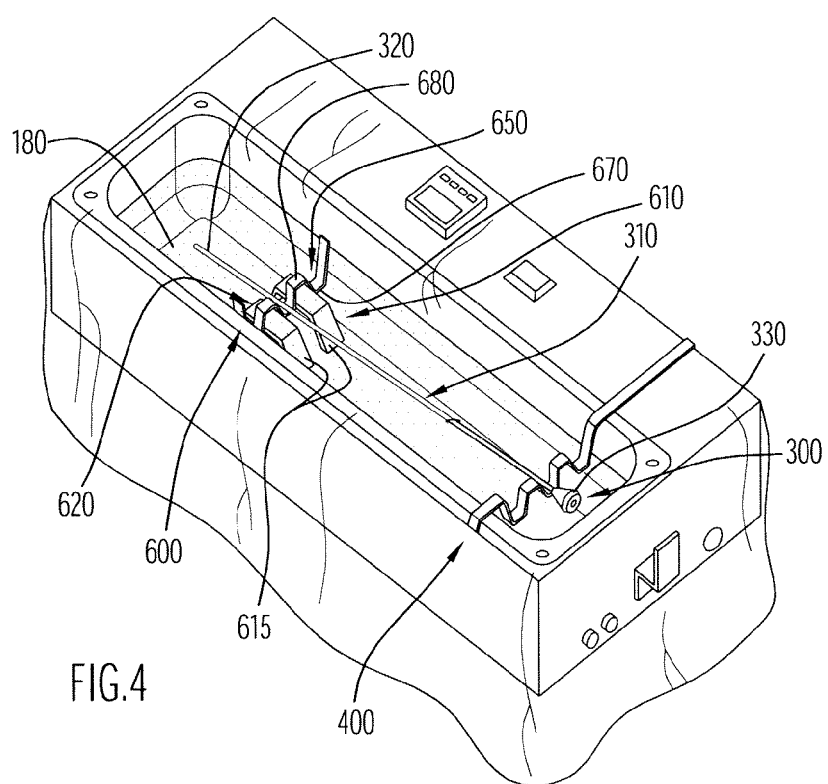
FIG. 4 illustrates a perspective view of a support assembly for a surgical instrument according to another embodiment of the invention, showing the support assembly coupled to the thermal treatment system of FIG. 1.

As shown in FIGS. 3 and 4, the first support rack 400 extends along the shorter dimension of the generally rectangular top surface 120 of the cabinet 105. The peaks 480 are generally level with the top surface 120 of cabinet 105, with the receptacles 450 extending below the rim of the basin 110. The recesses 450 may alternatively be configured to extend above the rim of the basin 110 (and thus above the cabinet top surface 120). The first end portion 420 and the second end portion 430 may be permanently or removably attached to the cabinet 105. For example, each end portion 420, 430 may comprise a generally U-shaped hook or engagement member configured to engage corresponding portions of the cabinet 105 located adjacent opposing larger dimensioned sides of the basin 110. The engagement members stably support the first support rack 400 on the system cabinet 105 to position the receptacles 450 above the fluid line of the thermal bath. In other words, the rack 400 basically rests on the cabinet portions and/or the basin lips or ledges and maintains the receptacles 450 above the sterile liquid 195 in the basin 110.

The second support member 500 may comprise a tray or rack configured to support the shaft 310 within the thermal bath such that the distal portion 320 of the shaft is elevated above the floor 180 of the basin 110. As seen in the embodiment illustrated in FIG. 3, the second support member 500 may comprise a rack including a bar having a first end portion 520, a second end portion 530, and an intermediate portion 540 including at least one receptacle 550 operable to receive a corresponding surgical scope 300. The second support rack 500 may be of any shape or size, and may include any number of receptacles 550. Similarly, the bar may be of any size, shape, or thickness suitable for its described function, and may include any suitable cross-sectional shape. By way of example, the bar may be a substantially flat bar with a substantially rectangular cross section. The receptacles 550 may each be of any shape suitable to secure the scope 300 within the liquid bath contained in the basin 110, while elevating scope distal portion 320 above the basin floor 180. By way of further example, the intermediate portion 540 may include a series of serpentine or undulate portions that form the receptacles 550. The undulate portions are formed by a series of alternating recesses 570 and peaks 580. The recesses 570 form the receptacles 550 that support the distal portions 320 of the corresponding scopes 300. The receptacles 550 may include dimensions slightly larger than those of the shaft member 310. As explained above, the receptacles 450 of the first support rack 400 may have dimensions smaller than those of optics unit 330, serving as a stop to help prevent the scope 300 from sliding into and engaging the basin 110. The second support rack 500 may be constructed of high-density polyethylene, ABS thermoplastic, metals (e.g., steel), propylene material, or any material that is capable of withstanding temperatures typically used in thermal treatment systems (e.g., at least about 160° F.) and is sufficiently rigid to hold objects placed thereon.

Referring to FIG. 3, the second support rack 500 extends along the shorter dimension of the generally rectangular top surface 120 of the cabinet 105 such that it is spaced from the first support rack 400. The peaks 580 of the second support rack 500 are generally positioned below the top surface 120 of cabinet 105. For example, the peaks may be positioned proximate the center height of a basin vertical wall 175. The receptacles 550, moreover, are generally positioned lower than the receptacles 450 of the first support rack 400. For example, the receptacles 580 may be positioned slightly above the floor 180 of the basin 110. The first end portion 520 and the second end portion 530 may be permanently or removably attached to the cabinet 105. For example, each end portion 520, 530 may comprise a generally U-shaped hook or engagement member configured to engage corresponding portions of the cabinet 105 located adjacent opposing larger dimensioned sides of the basin 110. The engagement members stably support the second support rack 500 on the system cabinet 105 to position the receptacles 550 below the fluid line of the thermal bath. In other words, the second support rack 500 basically rests on the cabinet portions and/or the basin lips or ledges and maintains the receptacles 550 below the surface (fluid line) of the sterile liquid 195 in the basin 110 and above the basin floor 180.

In operation, the portion of the shaft member 310 immediately distal of the optics unit 330 is placed in the receptacle 450 of the first support rack 400 to support the optics unit 330 above the surface or fluid line of the liquid bath. Similarly, the portion of the shaft immediately proximate of the shaft distal end is placed in the receptacle 550 of the second support rack 500 to support the shaft 310 above the basin floor 180 and away from the basin side walls 175. That is, when the scope 300 is placed on the support racks 400, 500, the shaft member 310 extends distally from the receptacle 450 of the first support rack 400, into the liquid bath, and to the receptacle 550 of the second support rack 500. Thus, the optics unit 330 rests on the racks in a dry state, while the scope shaft member 310 is primarily placed into the liquid bath (below the fluid line). The recesses 450, 550 stabilize the scope 300, preventing contact with the basin 110 (and specifically, the basin side walls 175 and floor 180). This allows for accurate temperature warming of selected portions of the scope, which, in turn, reduces tissue trauma, maintains normothermia, and enables the scope optics unit to remain dry for clear viewing of images. In addition, damage to any one or more of the scope 300, the basin 110, or the drape 170 is avoided since the second support rack 500 guards against the distal end of the scope contacting the basin with force sufficient to puncture the drape and/or damage the scope.

The position of first support rack 400 with respect to the second support rack 500 is not particularly limited. By way of example, and as shown in FIG. 3, the first support rack 400 may be positioned at or near the forward end or front half of basin 110, while the second support rack 500 may be positioned at or near the rearward end or back half of the basin 110. However, the support members 400, 500 may be positioned at any point along the cabinet and/or basin suitable to submerge at least a portion of the shaft member 310 into the liquid bath and support the distal portion 320 above the basin floor 180, while elevating the optics unit 330 above the bath to maintain the optics unit 330 in a dry state.

FIG. 4 is a perspective view of the thermal system 100 including a scope support assembly according to another embodiment of the invention. In the embodiment illustrated, the first support member 400 may include a rack similar to that described above. The second support member 600, however, may now comprise a stand operable to stabilize the distal portion 320 of the scope 300, supporting the shaft 310 away from the walls 175 and above the floor 180 and of the basin 110. The second support member 600 (also called a second support stand) may comprise a base 610 that supports a bar 620 including at least one receptacle 650 operable to receive a corresponding surgical scope 300. The stand 600 may be of any shape or size, and may include any number of receptacles 650. Similarly, the bar 620 may be of any size, shape, or thickness suitable for its described function, and may include any suitable cross-sectional shape. By way of example, the bar 620 may be a substantially flat bar with a substantially rectangular cross section. The receptacles 650 may each be of any shape suitable to secure the scope 300 within the liquid bath contained in the basin 110, while elevating scope distal portion 320 above the basin floor 180. By way of further example, the bar 610 may include a series of serpentine or undulate portions that form the receptacles 650. The undulate portions are formed by a series of alternating recesses 670 and peaks 680. The recesses 670 form the receptacles 650 that support the distal portion 320 of the corresponding scope 300. The receptacles 650 may include dimensions slightly larger than those of the shaft member 310. As explained above, the receptacles 450 of the first support rack 400 may have dimensions smaller than those of optics unit 330, serving as a stop to help prevent the scope 300 from sliding into the basin 110.

The base 610 may comprise one or more foot members 615 coupled to the bar 620. Each foot member 615 may be positioned near each peak 670 of the bar 620. The foot members 615 support the bar 610 above the floor 180 of the basin 110. The foot members 615 stably support the second support stand 600 in the basin 110 to position the receptacles 650 below the fluid line of the thermal bath. In other words, the second support stand 600 basically rests on the basin floor 180 and maintains the receptacles 650 below the surface (fluid line) of liquid bath in the basin 110 and above the basin floor 180. The second support stand 600 (the base 610 and/or bar 620) may be constructed of high-density polyethylene, ABS thermoplastic, metals (e.g., steel), propylene material, or any material that is capable of withstanding temperatures typically used in thermal treatment systems (e.g., at least about 160° F.) and is sufficiently rigid to hold objects placed thereon. In addition, the stand may be preformed into the drape 170.

The second support stand 600 is positioned within the basin 110 such that it is spaced from the first support member 400, with the bar 620 extending along the shorter dimension of the basin 110. The peaks 680 of the second support stand 600 are generally positioned below the top surface 120 of cabinet 105. For example, the peaks 680 may be generally aligned with the center height of the basin vertical walls 175. In addition, the receptacles 650 (i.e., the recesses 670) may be generally positioned lower than the receptacles 450 of the first support rack 400. For example, the receptacles 680 may be positioned slightly above the floor 180 of the basin 110. The position of first support rack 400 with respect to the second support stand 600 is not particularly limited. By way of example, and as shown in FIG. 4, the first support rack 400 may be positioned at or near the forward end or front half of basin 110, while the second support stand 600 may be positioned at or near the rear end or back half of the basin 110. However, the support members 400, 600 may be positioned at any point along the cabinet and/or basin suitable to submerge at least a portion of the shaft member 310 into the liquid bath and support the distal portion 320 above the basin floor 180, while elevating the optics unit 330 above the bath to maintain the optics unit 330 in a dry state.

In operation, the portion of the shaft member 310 immediately distal of the optics unit 330 is seated in the receptacle 450 of the first support rack 400 to support the optics unit 330 above the surface or fluid line of the liquid bath. Similarly, the portion of the shaft immediately proximate of the shaft distal end is seated in the receptacle 650 of the second support stand 600. That is, when the scope 300 placed on the first 400 and second support members 600, the shaft member 310 extends distally from the receptacle 450 of the first support rack 400, into the liquid bath, and to the receptacle 650 of the second support stand 600. While seated in the receptacles 450, 650, the scope 300 is stabilized. Thus, the optics unit 330 rests on the support members 400, 600 in a dry state, while the scope shaft member 310 is primarily placed into the liquid bath (below the fluid line) such that it does not engage the basin 110 (and specifically, the basin walls 175 and/or floor 180). This allows for accurate temperature warming of selected portions of the scope, which, in turn, reduces tissue trauma and enables the scope optics unit to remain dry for clear viewing of images. In addition, damage to any one or more of the scope 300, the basin 110, or the drape 170 is avoided since the second support stand 600 guards against the distal end of the scope contacting the basin with force sufficient to puncture the drape or damage the scope.

Figure 5:
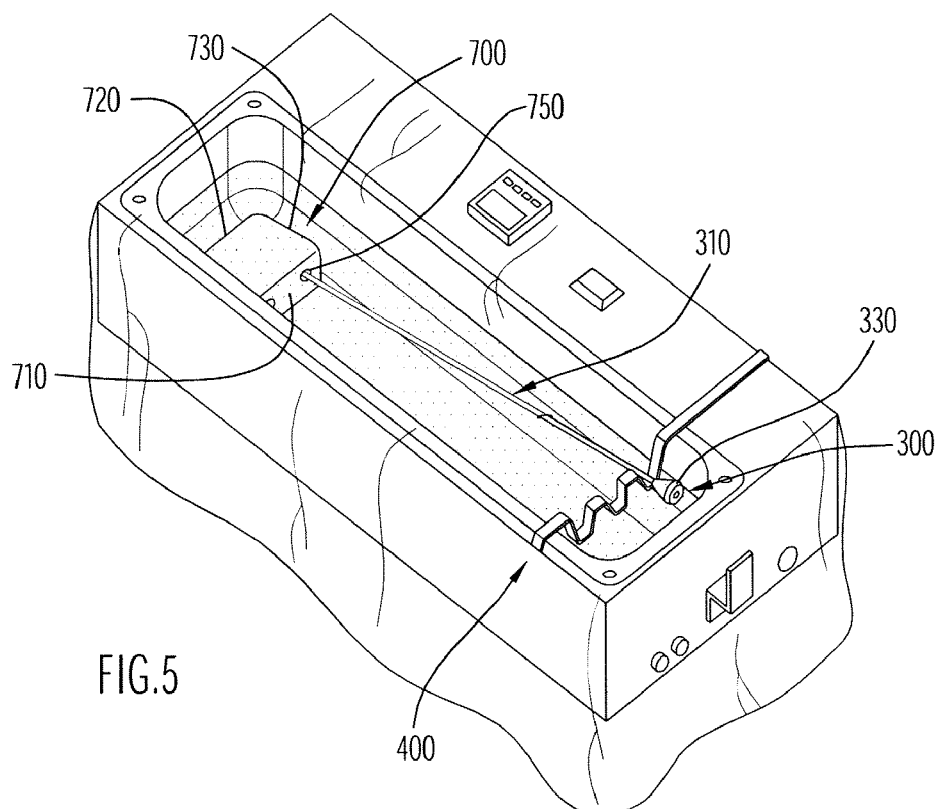
FIG. 5 illustrates a perspective view of a support assembly for a surgical instrument according to another embodiment of the invention, showing the support assembly coupled to the thermal treatment system of FIG. 1.

FIG. 5 is a perspective view of the thermal system 100 including a scope support assembly according to another embodiment of the invention. In the embodiment illustrated, the first support member 400 may include a rack similar to that described above. The second support member, however, may now comprise a block operable to stabilize the distal portion 320 of the scope 300, supporting the shaft 310 away from the walls 175 and above the floor 180 of the basin 110. The second support member 700 (also called a second support block) may comprise a generally rectangular, parallelepiped structure including a front wall 710, a rear wall 720, and opposed side walls 730. The second support block 700, however, may be of any shape or size suitable to its described function. For example, the block may include a triangular transverse cross section (i.e., the top and/or bottom walls of the block may slope with respect to the basin floor 180). The block 700 includes least one receptacle 750 operable to longitudinally receive a portion (e.g., the distal end or tip) of a corresponding surgical scope 300. The receptacles 750 may each be of any shape suitable to retain the scope 300 within the liquid bath contained in the basin 110, while elevating scope distal portion 320 away from the basin walls 175 and/or above the basin floor 180. By way of example, the receptacle 750 may comprise a bore or channel extending entirely through the block 700 (front to back); alternatively, the bore may extend partially through the block, having closed end at or near the rear of the block. In addition, the bores may angularly slope within the block (e.g., the bores may slope downward from the front wall 710 to the rear wall 720 to orient the receptacles upward toward the first support member 400). Thus, the bore forms the receptacle 750 that supports the distal portion 320 of the corresponding scope 300. The receptacle bores may include dimensions slightly larger than those of the scope shaft member 310 to permit insertion of the shaft 310 therein, as well the flow of fluid through the bores (to ensure fluid contact with the portion of the scope positioned within the receptacles 750). As explained above, the receptacles 450 of the first support rack 400 may have cross-sectional dimensions smaller than those of optics unit 330, serving as a stop to help prevent the scope 300 from sliding into the basin 110.

The second support block 700 rests on the basin floor 180 and maintains the receptacles 750 below the surface (fluid line) of the liquid bath in the basin 110 and above the basin floor 180. The support block 700 may be constructed of high-density polyethylene, ABS thermoplastic, metals (e.g., steel), propylene material, or any material that is capable of withstanding temperatures typically used in thermal treatment systems (e.g., at least about 160° F.) and is sufficiently rigid to hold or retain objects placed thereon or received therein. In addition, the block 700 may be preformed into the drape 170, or may be otherwise secured to drape so that the drape and block can be sold as an integral unit.

The second support block 700 is positioned within the basin 110 such that it is spaced from the first support member 400, with the receptacles 750 (i.e., the bores) of the second support block 700 generally positioned lower than the receptacles 450 of the first support rack 400. For example, the block may be configured to position the bores slightly above the floor 180 of the basin 110. The position of first support rack 400 with respect to the second support block 700 is not particularly limited. By way of example, and as shown in FIG. 5, the first support rack 400 may be positioned near or at a forward end or front half of basin 110, while the second support block 700 may be positioned at or near the rear end or rear half of the basin 110. The support members 400, 700, however, may be positioned at any point along the cabinet 105 and/or basin 110 suitable to submerge at least a retained portion of the shaft member 310 into the liquid bath and support the distal portion 320 above the basin floor 180, while elevating the optics unit 330 above the bath to maintain the optics unit 330 in a dry state.

In operation, the portion of the shaft member 310 immediately distal of the optics unit 330 is seated in the receptacle 450 of the first support rack 400 to support the optics unit 330 above the surface (fluid line) of the liquid bath. The distal end 320 of the shaft 310 is inserted into the receptacle 750 of the second support block 700 such that it is seated within the bore (preferably, the shaft does not extend beyond the back wall 720 of the block). Thus, when the scope 300 is placed on the first 400 and second support members 700, the scope shaft member 310 extends distally from the receptacle 450 of the first support rack 400, into the liquid bath, and to the receptacle 750 of the second support block. While seated in the receptacles 450, 750, the scope 300 is stabilized. Thus, the optics unit 330 rests on the support members 400, 700 in a dry state, while the scope shaft member 310 is primarily placed into the liquid bath such that it does not engage the basin 110 (and specifically, the basin walls 175 and/or floor 180). This allows for accurate temperature warming of selected portions of the scope, which, in turn, reduces tissue trauma and enables the scope optics unit to remain dry for clear viewing of images. In addition, damage to any one or more of the scope 300, the basin 110, or the drape 170 is avoided since the second support block 700 guards against the distal end of the scope contacting the basin with force sufficient to puncture the drape or damage the scope.

Figure 6:
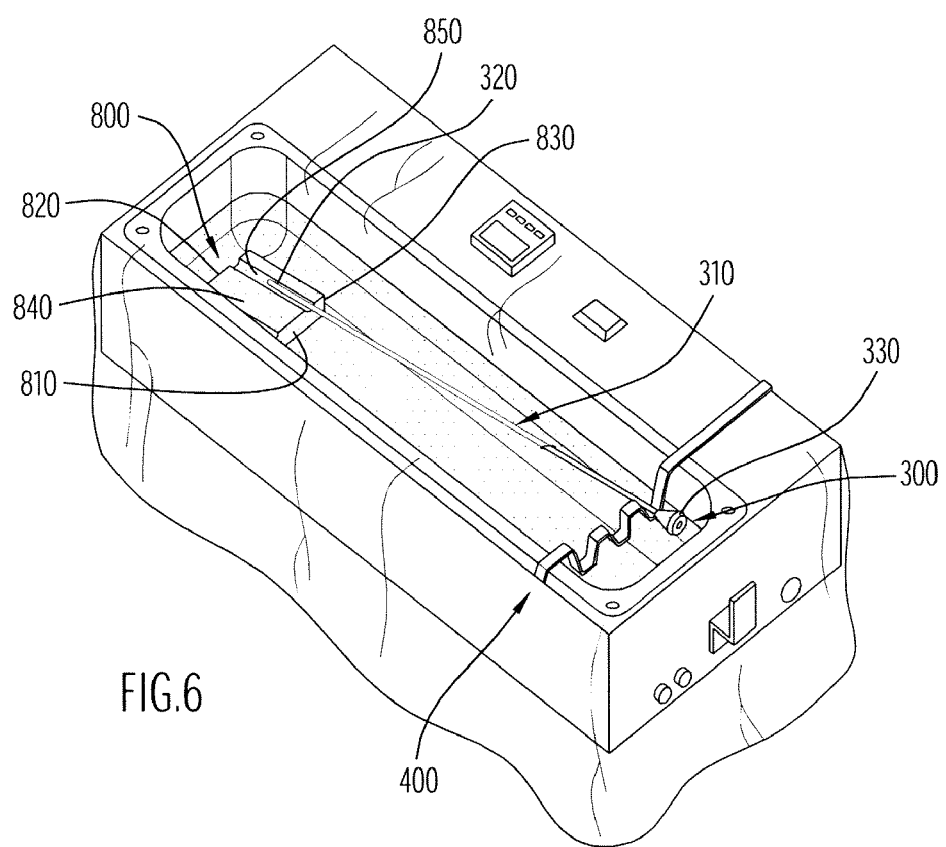
FIG. 6 illustrates a perspective view of a support assembly for a surgical instrument according to another embodiment of the invention, showing the support assembly coupled to the thermal treatment system of FIG. 1.

FIG. 6 is a perspective view of the thermal system 100 including a scope support assembly according to another embodiment of the invention. In the embodiment illustrated, the first support member 400 may include a rack similar to that described above. The second support member, however, may now comprise a platform operable to stabilize the distal portion 320 of the scope 300, supporting the shaft 310 away from the walls 175 and above the floor 180 and of the basin 110. The second support member 800 (also called a second support platform) may comprise a generally rectangular, parallelepiped structure including a front wall 810, a rear wall 820, opposed side walls 830, and a top surface 840. The second support platform 800, however, may be of any shape or size suitable to its described function. For example, the platform 800 may include a triangular transverse cross section (i.e., the top and/or bottom walls of the platform may slope with respect to the basin floor 180 such that the front end of the platform is thicker than the back end of the platform). By way of specific example, the top surface 840 of the platform may slope downward from the front wall 810 to the rear wall 820 to orient the receptacles upward toward the first support member 400. The platform 800 includes least one receptacle 850 operable to receive a corresponding surgical scope 300. The receptacles 850 may each be of any shape suitable to receive the scope 300 within the liquid bath contained in the basin 110, while elevating scope distal portion 320 away from the basin walls 175 and/or above the basin floor 180. By way of further example, the support platform 800 includes at least one open groove or slot defined in the top surface 840 that extends from the front platform wall 810 (the wall facing the first support member) to the rear platform wall 820. The open grooves form the receptacles 850 that support the distal portion 320 of the corresponding scope 300. The open grooves may extend completely or partially across the top surface 840 of the platform 800. The receptacles 850 may include dimensions slightly larger than those of the scope shaft member 310. As explained above, the receptacles 450 of the first support rack 400 may have dimensions smaller than those of optics unit 330, serving as a stop to help prevent the scope 300 from sliding into the basin 110.

The second support platform 800 rests on the basin floor 180 and maintains the receptacles 850 below the surface (fluid line) of liquid bath in the basin 110 and above the basin floor 180. The support platform 800 may be constructed of high-density polyethylene, ABS thermoplastic, metals (e.g., steel), propylene material, or any material that is capable of withstanding temperatures typically used in thermal treatment systems (e.g., at least about 160° F.) and is sufficiently rigid to hold objects placed thereon. In addition, the platform 800 may be preformed into or otherwise secured to the drape 170.

The second support platform 800 is positioned within the basin 110 such that it is spaced from the first support member 400, with the receptacles 850 (i.e., the grooves) of the second support platform 800 generally positioned lower than the receptacles 450 of the first support rack 400. For example, the grooves may be positioned within the platform such that they are slightly above the floor 180 of the basin 110. The position of first support rack 400 with respect to the second support platform 800 is not particularly limited. By way of example, and as shown in FIG. 6, the first support rack 400 may be positioned near or at the forward end or front half of basin 110, while the second support platform 800 may be positioned at or near the rearward end or at rear half of the basin 110. The support members 400, 800, however, may be positioned at any point along the cabinet and/or basin 110 suitable to submerge at least a portion of the shaft member 310 into the liquid bath and support the distal portion 320 above the basin floor 180, while elevating the optics unit 330 above the fluid line of the bath to maintain the optics unit 330 in a dry state.

In operation, the portion of the shaft member 310 immediately distal of the optics unit 330 is seated in the receptacle 450 of the first support rack 400 to support the optics unit 330 above the surface (fluid line) of the liquid bath. The distal end 320 of the shaft 310 is inserted into the receptacle 850 of the second support platform 800 such that it is seated within the groove (preferably, the shaft does not extend beyond the back wall 820 of the platform). Thus, when the scope 300 is placed on the first 400 and second 800 support members, the shaft member 310 extends distally from the receptacle 450 of the first support rack 400, into the liquid bath, and to the receptacle 850 of the second support platform 800. While seated in the receptacles 450, 850, the scope 300 is stabilized. Thus, the optics unit 330 rests on the support members 400, 800 in a dry state, while the scope shaft member 310 is primarily placed into the liquid bath such that it does not engage the basin 110 (and specifically, the basin walls 175 and/or floor 180). This allows for accurate temperature warming of selected portions of the scope, which, in turn, reduces tissue trauma and enables the scope optics unit to remain dry for clear viewing of images. In addition, damage to any one or more of the scope 300, the basin 110, or the drape 170 is avoided since the second support platform 800 guards against the distal end of the scope contacting the basin with force sufficient to puncture the drape or damage the scope.

Operation of the system is now more fully described with reference to FIGS. 1-6. Specifically, the drape 170 may be disposed over the cabinet 105 and within the basin 110 to form a drape receptacle as described above. The first support member 400 may be disposed on the cabinet 105 near the front end of the basin 110. The first support member 400 may be disposed above (FIGS. 3-6) or below (FIGS. 7-8) drape 170 to engage scopes placed within the basin. When the first support member 400 is disposed below the drape 170, a portion of the drape may be pushed down into each receptacle 450. Similarly, the second support member 500 may be disposed on the cabinet 105 near the back end of the basin 110. Alternatively, the second support member stand 600, block 700, or platform 800 may be set on the floor 180 of the basin proximate its back end. The second support member 500, 600, 700, 800 may be disposed above (FIGS. 3-6) or below (FIGS. 7-8) the drape 170 to engage any scopes placed within the basin 110. When the second support member 500, 600, 700, 800 is disposed below the drape 170, a portion of the drape may be pushed down into each receptacle 550, 650, 750, 850.

The basin 110 is filled with a sterile liquid 195 and a scope 300 is positioned in the receptacle 450 of the first support member 400, as well in the receptacle 550, 650, 750, 850 of the second support member 500, 600, 700, 800. When placed on the first 400 and second 500, 600, 700, 800 support members, the distal portion 320 of the scope is submerged in the liquid bath and the scope optics unit 330 is elevated above the bath and/or above the basin 110 as described above. In addition, the distal portion 320 is elevated above the floor 180 of the basin 110 such that no portion of the scope contacts the basin. The bath may then be heated to the desired temperature via manipulation of the controller 130. Alternatively, the bath may be heated before the scope 300 is positioned in the support members 400, 500, 600, 700, 800. The scope 300 absorbs the proper amount of thermal energy from the liquid bath in basin 110, while the optics unit 330 of the scope 300 remains dry, thereby preventing image distortion caused by liquid contacting exposed optics.

The first 400 and second 500, 600, 700, 800 support members may be a separate unit as described above, or alternatively, may be formed integral with drape 170. In this case, the support members 400, 500, 600, 700, 800 may be attached to the drape by use of ultrasonic energy, heat welding, solvents, adhesives, RF welding techniques or any other appropriate or conventional attachment process. The support members 400, 500, 600, 700, 800 may be formed on the drape 170 such that the support members 400, 500, 600, 700, 800 correspond to and indicate the approximate edges of the basin 110 for proper placement of the drape 170 on the thermal treatment system 100. The drape 170 is disposed on the cabinet 105 such that portions of the drape are pushed down into, and conform to, the basin 110 to form a drape receptacle, with the first support member 400 positioned within the basin above the basin floor 180, and the second support member 500, 600, 700, 800 positioned lower with respect to the first support member 400. The remaining portions of the drape 170 cover the top surface 120 and hang down the sides of cabinet 105. The drape receptacle typically contains a heated liquid bath, while the receptacles 450, 550, 650, 750, 850 of the support members 400, 500, 600, 700, 800 receive and support the scope 300 with the optics unit 320 elevated above the sterile liquid 195 and the distal portion 320 elevated above the basin floor 180 but within the liquid bath as described above.

It will be appreciated that the embodiments described above and illustrated in the drawings represent only a few of the many ways of implementing a thermal treatment system instrument rack and method of selectively thermally treating medical instrument portions. For example, the present invention support members and/or thermal treatment systems are not limited to the applications described herein, but may be utilized for any types of medical or other items to selectively thermally treat any portions of those items.

In addition, the warming, cooling, and plural basin systems and their corresponding cabinets, assemblies or housings may be of any shape or size and may be constructed of any suitable materials. The plural basin system may include any quantity of heating and/or cooling basins in any combinations. The basins of the systems may be of any shape or size, may be constructed of any suitable thermal conducting materials (e.g., stainless steel, etc.), and may be disposed at any suitable locations on or within the housings. The systems may include any conventional or other heating and/or refrigeration units to thermally treat any type of sterile medium or other substance to any desired temperature. The heating unit may include any conventional or other heating device and components to control heating of a basin to any desired temperature (e.g., preferably to temperatures near (e.g., above, at or below) body temperature, such as temperatures in the approximate range of 60° F.-160° F.). The heater element may be of any quantity (e.g., at least one), shape or size, and may include any configuration (e.g., strips, bars, segments, etc.) that covers the entirety or any portion of a basin. The heater element may be attached to a basin via any conventional or other fastening techniques (e.g., any type of adhesives, brackets, etc.). In addition, the heater element may be implemented by any conventional or other type of heater or heating element (e.g., heating coils, etc.) that may be disposed on or proximate a basin at any suitable locations.

A cooling unit may include any conventional or other cooling or refrigeration device and components to control cooling of a basin to any desired temperature (e.g., preferably to temperatures near or below the freezing temperature of the sterile liquid or medium, such as temperatures in the approximate range of −32° F. to 32° F.). The various power switches and controllers of the systems may be implemented by any conventional or other power and control devices and may be disposed on the systems at any suitable locations.

The temperature sensor may be implemented by any conventional or other temperature sensing device (e.g., infrared, RTD, etc.) and may be disposed at any location on or proximate a basin or within the systems. The basins of the systems may be disposed in any arrangement or at any suitable locations on the systems. The systems may thermally treat (e.g., heat or cool) any type of medium or liquid, while a cooling basin may further include any type of conventional or other dislodgement mechanism, such as those described in the aforementioned patents.

The drapes employed with the heating, cooling and plural basin systems may be of any size or shape, and may be constructed of any suitable materials. The drapes are preferably transparent or translucent to facilitate manipulation of controls through the drape; however, these drapes may have any degree of transparency (e.g., including opaque). The drapes may be manipulated in any fashion with any portions of the drapes serving as a drape receptacle within a corresponding basin. The drapes may be of sufficient size to accommodate and form drape receptacles within any quantity of thermal treatment system basins. The drape may facilitate placement of any types of objects (e.g., instruments, containers, etc.) within the basin.

The support members may be of any quantity, size or shape, may be disposed on any part of the drape or cabinet and may be constructed of any suitable materials. The support members may be a separate unit or formed integral with and/or attached to the drape and/or preformed container portion via ultrasonic energy, heat welding, solvents, adhesives, RF welding techniques or any other attachment process. The support members may be any device capable of elevating objects above the basin floor and may be disposed in the basins above or below the drape. The support members may include any quantity of receptacles each to accommodate any quantity or portions of scopes or other objects. The support members may include any configuration (e.g., serpentine, rings, linear, dividers, etc.) to form receptacles of any quantity, shape or size to receive any medical or other objects. The basin may include any quantity of support members disposed at any locations to elevate and/or submerge any portions of medical or other items. The support members may include any quantity of any types of engagement mechanisms (e.g., clamps, brackets, hook and loop fasteners, adhesives, etc.) of any shape or size and disposed at any locations to engage the basin and/or cabinet. The support members may be configured to accommodate any quantity of basins. For example, the support members may be configured for placement in and to accommodate scopes within two or more adjacent basins.

The control circuit, power port, fuse holders, and/or other components may be disposed within the systems at any suitable locations and may be implemented by any conventional or other circuitry components arranged in any desired fashion to perform the described functions. The temperature controller may be implemented by any conventional or other temperature controller and include any desired devices for entering a temperature (e.g., buttons, keypad, etc.). The basin power switch of the systems may be implemented by any conventional or other switching device, while the fuses may be implemented by any conventional fuse or other limiting device and may be configured for any current or voltage levels. The power cord may be implemented by any conventional or other cord or cable and be configured to accommodate any desired power signals. The system may utilize any type of power source (e.g., batteries, wall outlet jack, AC, DC, etc.).

It is to be understood that the terms "top", "bottom", "front", "rear", "side", "height", "length", "width", "upper", "lower", "vertical" and the like are used herein merely to describe points of reference and do not limit the present invention to any particular orientation or configuration.

From the foregoing description, it will be appreciated that the invention makes available a novel thermal treatment system instrument support members and method of selectively thermally treating medical instrument portions, wherein a system warms surgical scopes in a temperature controlled liquid bath while maintaining optics of the scope in a dry state.

Having described preferred embodiments of a new and improved thermal treatment system instrument rack and method of selectively thermally treating medical instrument portions, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A thermal treatment system for thermally treating an object including a medical instrument comprising:
   a housing including a top surface;
   a basin recessed into said top surface and configured to contain a sterile medium, wherein said basin comprises a floor;
   a thermal unit to thermally treat said basin and said sterile medium;
   a first support disposed to rest at least partially on the housing top surface and having a portion defining at least one upper receptacle within said basin to support the object, wherein the at least one upper receptacle is positioned at least partially above said sterile medium at a first elevation relative to said basin floor; and
   a second support disposed within said basin and having a portion defining at least one lower receptacle within said basin to support the object, wherein the at least one lower receptacle is positioned at least partially below the surface of the sterile medium at a second elevation relative to said basin floor that is lower than said first elevation, wherein the at least one upper receptacle and the at least one lower receptacle are configured to support the object including the medical instrument within the basin at an inclined angle relative to said basin floor such that a portion of the object is elevated above the surface of the sterile medium to maintain that portion in a dry state.

2. The thermal treatment system of claim 1, wherein the first support comprises a rack including a first end portion, a second end portion, and an intermediate portion defining the at least one upper receptacle.

3. The thermal treatment system of claim 2, wherein the intermediate portion of the first support comprises a series of alternating recesses and peaks disposed perpendicularly to said basin floor, and wherein the recesses define a series of upper receptacles.

4. The thermal treatment system of claim 2, wherein each of the end portions of the first support comprise an engagement member configured to engage the housing top surface and position the first support proximate the housing top surface.

5. The thermal treatment system of claim 1, wherein the second support comprises a rack including a first end portion, a second end portion, and an intermediate portion defining the at least one lower receptacle to support the object.

6. The thermal treatment system of claim 5, wherein the intermediate portion of the second support comprises a series of alternating recesses and peaks disposed perpendicularly to said basin floor, and wherein the recesses define a series of lower receptacles.

7. The thermal treatment system of claim 5, wherein the end portions of the second support member each comprise an engagement member configured to engage the housing top surface and position the second support proximate the basin floor.

8. The thermal treatment system of claim 1, wherein the second support comprises a stand including a base disposed on said basin floor that supports a portion defining a lower receptacle.

9. The thermal treatment system of claim 8, wherein the second support receptacle defining portion comprises a series of alternating recesses and peaks, and wherein the recesses define a plurality of lower receptacles.

10. The thermal treatment system of claim 1, wherein the second support comprises a block with at least one lower receptacle configured to receive a portion of the object.

11. The thermal treatment system of claim 10, wherein the lower receptacle is formed by a bore extending through the block.

12. The thermal treatment system of claim 1, wherein the second support comprises a platform disposed on said basin floor with at least one longitudinal lower receptacle configured to longitudinally support a portion of the object.

13. The thermal treatment system of claim 12, wherein the longitudinal lower receptacle comprises an open slot defined in a top surface of the platform.

14. The thermal treatment system of claim 1, wherein the object includes a surgical scope with a distal portion and a proximal portion including an optics unit.

15. The thermal treatment system of claim 14, wherein the first and second supports maintain the optics unit in a dry state by positioning the scope distal portion in the sterile medium and elevating the scope optics unit above the sterile medium.

16. The thermal treatment system of claim 1, further comprising a drape disposed over the thermal treatment system and recessed within said basin to form a drape receptacle for said sterile medium.

17. The thermal treatment system of claim 16, wherein the first and second supports are disposed above the drape.

18. The thermal treatment system of claim 16, wherein the first and second supports are disposed below the drape.

19. The thermal treatment system of claim 16, wherein the first and second supports are formed integral with the drape.

20. The thermal treatment system of claim 16, wherein the drape includes sensors to detect at least one of the presence of a liquid within the basin, the absence of a liquid within the basin, or the presence of a drape leak.

21. In a thermal treatment system including a housing with a top surface, a basin recessed into said top surface including a floor and configured to contain a sterile medium, a first support disposed to rest at least partially on the housing top surface and having a portion defining at least one upper receptacle positioned within said basin and above said sterile medium, a second support disposed within said basin and having a portion defining at least one lower receptacle positioned at least partially below the surface of the sterile medium, a method of selectively thermally treating medical instrument portions comprising:
  (a) receiving an object including a medical instrument within said basin with a first portion of said object supported by the at least one upper receptacle of the first support at a first elevation relative to the basin floor to maintain the first portion in a dry state and a second portion of the object supported by the at least one lower receptacle of the second support above the floor of the basin at a second elevation relative to the basin floor lower than said first elevation to thermally treat the second portion via the sterile medium, wherein the object is supported within the basin at an inclined angle relative to the basin floor.

22. The method of claim 21, wherein the object includes a surgical scope including a distal portion and a proximal portion with an optics unit, and step (a) further includes:
  (a.1) receiving said object on the supports such that the distal portion contacts the sterile medium and the optics unit is elevated above said sterile medium.

23. The method of claim 21, wherein the first and second supports each comprise a serpentine portion with at least one peak and at least one recess forming a corresponding receptacle disposed perpendicularly to said basin floor, and step (a.1) further includes:
  (a.1.1) receiving the object within the upper and lower receptacles of the first and second supports such that the distal portion extends from the upper receptacle into the sterile medium and to the lower receptacle.

24. A surgical drape for use in a thermal treatment system including a housing with a top surface and a basin recessed within the housing top surface to contain and thermally treat a sterile medium, the basin including a floor, said drape comprising:
  a drape adapted to cover and hang down from the top surface of the housing, the drape being disposed within and conforming to the basin to form a drape receptacle;
  a first support disposed to rest at least partially on the housing top surface and within the drape receptacle at a first elevation relative to said basin floor and having a portion defining at least one upper receptacle configured to removably receive and support a first portion of an object including a medical instrument above the surface of the sterile medium to maintain the first object portion in a dry state; and
  a second support disposed within the drape receptacle and having a portion defining at least one lower receptacle at a second elevation relative to said basin floor that is lower than said first elevation, wherein the at least one lower receptacle is configured to support a second portion of the object below the surface of the sterile medium and above the floor of the basin, wherein the at least one upper receptacle and the at least one lower receptacle are further configured to support the object including the medical instrument within the basin at an inclined angle relative to said basin floor.

25. The drape of claim 24, wherein
  the first support is in the form of a rack comprising a first end portion configured to engage said housing; a second end portion configured to engage the housing; and an intermediate portion defining the at least one upper receptacle; and
  the second support is in the form of a rack comprising a first end portion configured to engage said housing; a second end portion configured to engage the housing; and an intermediate portion including at least one lower receptacle configured to removably receive the object.

26. The drape of claim 25, wherein each of the intermediate portions include a series of alternating peaks and recesses disposed perpendicularly to said basin floor, and wherein the recesses respectively form the at least one upper and lower receptacles.

27. The drape of claim 24, wherein
  the first support is in the form of a rack comprising a first end portion configured to engage said housing; a second end portion configured to engage the housing; and an intermediate portion defining the at least one upper receptacle; and
  the second support is in the form of a stand comprising a base disposed on said basin floor and a bar supported by the base, the bar comprising at least one lower receptacle configured to removably receive the object.

28. The drape of claim 27, wherein
  the first support intermediate portion includes a series of alternating peaks and recesses, and wherein the recesses form the at least one upper receptacle; and
  the second support bar includes a series of alternating peaks and recesses, and wherein the recesses form the at least one lower receptacle.

29. The drape of claim 24, wherein
  the first support is in the form of a rack comprising a first end portion configured to engage said housing; a second end portion configured to engage the housing; and an intermediate portion defining the at least one upper receptacle; and the second support comprises a platform disposed on said basin floor including a longitudinal lower receptacle formed by a slot extending along the top surface of the platform.

30. The drape of claim 24, wherein the first support is in the form of a rack comprising a first end portion configured to engage said housing; a second end portion configured to engage the housing; and an intermediate portion defining the at least one upper receptacle; and the second support comprises a block including a lower receptacle formed by a channel extending through the block.

31. The drape of claim 24, wherein the object includes a scope with an optics unit.

32. The drape of claim 24, wherein the drape further includes sensors to detect at least one of the presence of a liquid within the basin, the absence of a liquid within the basin, or the presence of a drape leak.

* * * * *